(12) United States Patent
Kanzaki et al.

(10) Patent No.: US 9,889,228 B2
(45) Date of Patent: Feb. 13, 2018

(54) CULTURED CELL SHEET, PRODUCTION METHOD, AND TISSUE REPAIR METHOD USING THEREOF

(71) Applicant: CELLSEED INC., Tokyo (JP)

(72) Inventors: Masato Kanzaki, Tokyo (JP); Masayuki Yamato, Tokyo (JP); Tinatsu Kohno, Machida (JP); Hidekazu Sekine, Kasukabe (JP); Akihiko Kikuchi, Tokyo (JP); Teruo Okano, Ichikawa (JP); Takamasa Onuki, Yokohama (JP)

(73) Assignee: CELLSEED INC., Tokyo (JP)

( * ) Notice: Subject to any disclaimer, the term of this patent is extended or adjusted under 35 U.S.C. 154(b) by 44 days.

(21) Appl. No.: 14/228,212

(22) Filed: Mar. 27, 2014

(65) Prior Publication Data

US 2014/0212470 A1    Jul. 31, 2014

Related U.S. Application Data

(62) Division of application No. 11/885,222, filed as application No. PCT/JP2006/303762 on Feb. 28, 2006, now abandoned.

(30) Foreign Application Priority Data

Feb. 28, 2005 (JP) ................. 2005-096011

(51) Int. Cl.
| | |
|---|---|
| *A61L 27/38* | (2006.01) |
| *A61L 27/34* | (2006.01) |
| *C12N 5/00* | (2006.01) |
| *C12N 5/071* | (2010.01) |

(52) U.S. Cl.
CPC ........... *A61L 27/3895* (2013.01); *A61L 27/34* (2013.01); *A61L 27/3804* (2013.01); *A61L 27/3839* (2013.01); *C12N 5/0068* (2013.01); *C12N 5/0688* (2013.01); *C12N 2533/30* (2013.01)

(58) Field of Classification Search
CPC .. A61L 27/34; A61L 27/3804; A61L 27/3839; A61L 27/3895; C12N 5/0068; C12N 2533/30; C12N 5/0688
See application file for complete search history.

(56) References Cited

U.S. PATENT DOCUMENTS

| 4,944,941 | A | 7/1990 | Ammann |
|---|---|---|---|
| 5,284,766 | A | 2/1994 | Okano et al. |
| 6,956,077 | B1 | 10/2005 | Akiyama et al. |
| 7,470,424 | B2 | 12/2008 | Kataoka et al. |
| 7,691,369 | B2 | 4/2010 | Kataoka et al. |
| 2002/0032463 | A1 | 3/2002 | Cruise et al. |
| 2003/0036196 | A1 | 2/2003 | Okano et al. |
| 2004/0009566 | A1 | 1/2004 | Okano et al. |
| 2004/0028657 | A1 | 2/2004 | Okano et al. |
| 2004/0092492 | A1 | 5/2004 | Ring et al. |
| 2004/0197907 | A1 | 10/2004 | Kataoka et al. |
| 2006/0234377 | A1 | 10/2006 | Okano et al. |
| 2006/0240400 | A1 | 10/2006 | Yamato et al. |
| 2006/0240552 | A1 | 10/2006 | Yamato et al. |
| 2007/0015277 | A1 | 1/2007 | Hattori et al. |
| 2007/0092492 | A1 | 4/2007 | Matsuda et al. |
| 2007/0148137 | A1 | 6/2007 | Okano et al. |
| 2008/0118474 | A1 | 5/2008 | Okano et al. |
| 2008/0131476 | A1 | 6/2008 | Kanzaki et al. |
| 2008/0226692 | A1 | 9/2008 | Sato et al. |
| 2008/0227203 | A1 | 9/2008 | Watanabe et al. |
| 2008/0289052 | A1 | 11/2008 | Okano et al. |
| 2009/0011504 | A1 | 1/2009 | Kataoka et al. |
| 2011/0229962 | A1 | 9/2011 | Mizutani et al. |
| 2012/0052524 | A1 | 3/2012 | Kinooka et al. |
| 2012/0107930 | A1 | 5/2012 | Sasaki et al. |
| 2012/0156781 | A1 | 6/2012 | Takahashi et al. |
| 2012/0210451 | A1 | 8/2012 | Shimizu et al. |
| 2014/0212470 | A1 | 7/2014 | Kanzaki et al. |

FOREIGN PATENT DOCUMENTS

| EP | 0382214 | 8/1990 |
|---|---|---|
| EP | 1302535 | 4/2003 |
| JP | 03-500768 | 2/1991 |
| JP | 05-192138 | 8/1993 |

(Continued)

OTHER PUBLICATIONS

Herget et al. "Experimental use of an albumin-glutaraldehyde tissue adhesive for sealing pulmonary perenchyma and bronchial anastomoses", European Journal of Cardio-thoracic Surgery, 2001, vol. 19, pp. 4-9.*
Isaka et al. "Novel technique for sealing a lung air leak by using a skin fibroblast cell sheet, and an artificial organ" *Artificial Organ* vol. 33, No. 2, p. S-138 (Sep. 2004) and partial English translation.
Kanzaki et al. "Preparation of a cell sheet of lung cells by using a temperature-ressponsive culture dish and application of the cell sheet to sealing air leak" *J. Jpn. Assoc. Chest Surg.* vol. 18, p. 330, V-069 (Apr. 2004) and partial English translation.
Kanzaki et al. "Development of a novel air leak sealant with cell sheet engineering" *Clin. Pharmacol. Therap.* vol. 15, pp. 44-45 (Jan. 2005).
Kanzaki et al. "A cell sheet of skin fibroblasts prepared by using a culture medium supplemented by β-aminopropylnitrile" *Regenerative Med.* vol. 4, p. 94, WS-4-3 (Feb. 2005) and partial English translation.

(Continued)

*Primary Examiner* — Satyendra K Singh
(74) *Attorney, Agent, or Firm* — Nixon & Vanderhye P.C.

(57) ABSTRACT

The problem to be solved by the present invention is to provide a cultured cell sheet having a superior tissue adhesiveness and an excellent flexibility. The problems can be solved by producing the cultured cell sheet in which cells are cultured in the presence of a surfactant protein or a cross-linking inhibitor on a surface of a cell culture support that is coated with a temperature responsive polymer having an upper or lower critical solution temperature ranging from 0° C. to 80° C. in water, including steps of: adjusting the temperature of the culture medium to a temperature below the lower critical solution temperature or above the upper critical solution temperature; and detaching the cultured cell sheet.

5 Claims, 6 Drawing Sheets

(56) References Cited

FOREIGN PATENT DOCUMENTS

| JP | 2003-038170 | 2/2003 |
|---|---|---|
| WO | 89/01341 | 2/1989 |
| WO | 02/08387 | 1/2002 |
| WO | 02/10349 | 2/2002 |
| WO | 2005/011524 | 2/2005 |
| WO | 2006/093153 | 8/2006 |

OTHER PUBLICATIONS

Matsumoto et al. "Preparation of lung sheet by a temperature-responsive culture dish and trial for sealing air leak by the cell sheet" *Jpn. J. Thorac. Cardiovasc. Surg.* vol. 52, p. 548, LP3-39 (Sep. 2004) and partial English translation.

Cheng et al. "Novel cell patterning using microheater-controlled thermoresponsive plasma films" *J. Biomedical Materials Res.* 70A:159-168 (May 2004).

Contri et al. "Elastin-proteoglycans association revealed by cytochemical methods" *Connective Tissue Res.* 13:237-249 (1985).

Hirose et al. "Temperature-responsive surface for novel co-culture systems of hepatocytes with endothelial cells: 2-D patterned and double layered co-cultures" *Yonsei Med. J.* 41:803-813 (Dec. 2000).

Kanzaki et al. "Ondo Otosei Baiyozara ni yoru Hai Saibo Sheet Sakusei to Kiro Heisa eno Saibo Sheet no Oyo" *J. Jpn. Assoc. Chest Surg.* 18:330 (Apr. 2004).

Kanzaki et al. "Development of a novel air leak sealant with cell sheet engineering" *Clin. Pharmacol. Therap.* 15:44-45 (Jan. 2005).

Kanzaki et al. "β-aminopropylnitrile Tenka Baiyo ni yori Sakusei shita Hifu Shen'iga Saibo Sheet" *Regenerative Med.* 4:94 (Feb. 2005).

Kikuchi et al. "Two-dimensional manipulation of confluently cultured vascular endothelial cells using temperature-responsive poly(N-isopropylacrylamide)-grafted surfaces" *J. Biomaterials Sci. Polymer Ed.* 9:1331-1348 (Jan. 1998).

Levene & Carrington "The inhibition of protein-lysine 6-oxidase by various lathyrogens: Evidence for two different mechanisms" *Biochem. J.* 232:293-296 (Nov. 1985).

Matsumoto et al. "Ondo Otosei Baiyozara ni yoru Hai Saibo Sheet Sakusei to Saibo Sheet ni yoru Kiro Heisa no Kokoromi" *Jpn. J. Thorac. Cardiovasc. Surg.* 52:548 (Sep. 2004).

Maya et al. "Mitogenic response of rat lung and tracheal epithelial cells in monolayer primary cultures—Modulation of TNF-α expression" *J. Biosci.* 19:207-218 (Jun. 1994).

Nandkumar et al. "Two-dimensional cell sheet manipulation of heterotypically co-cultured lung cells utilizing temperature-responsive culture dishes results in long-term maintenance of differentiated epithelial cell functions" *Biomaterials* 23:1121-1130 (Feb. 2002).

Okano et al. "Mechanism of cell detachment from temperature-modulated, hydrophilic-hydrophobic polymer surfaces" *Biomaterials* 16:297-303 (Jan. 1995).

Shimizu et al. "Cell sheet engineering for myocardial tissue reconstruction" *Biomaterials* 24:2309-2316 (Jun. 2003).

Shimizu et al. "Fabrication of pulsatile cardiac tissue grafts using a novel 3-dimensional cell sheet manipulation technique and temperature-responsive cell culture surfaces" *Circulation Res.* 90:e40-e48 (Feb. 2002).

Tang et al. "Reaction of aortic lysyl oxidase with β-aminopropionitrile" *J. Biol. Chem.* 258:4331-4338 (Apr. 1983).

Ye et al. "Tissue engineering in cardiovascular surgery: New approach to develop completely human autologous tissue" *Eur. J. Cardiothor. Surg.* 17:449-454 (Apr. 2000).

Int'l Search Report for PCT/JP2006/303762, three pages, dated May 23, 2006.

Int'l Preliminary Report on Patentability (English translation) for PCT/JP2006/303762, six pages, dated Sep. 11, 2007.

Supplementary European Search Report for related EP 06714891.6, 11 pages, dated Oct. 5, 2012.

* cited by examiner

[Figure 1]

Bar = 100 μm

magnified view

[Figure 10]

magnified view

CULTURED CELL SHEET, PRODUCTION METHOD, AND TISSUE REPAIR METHOD USING THEREOF

This application is a divisional of application Ser. No. 11/885,222, filed Aug. 28, 2007, pending; which is the U.S. national stage of Application No. PCT/JP2006/303762, filed Feb. 28, 2006; which claims the benefit of Japanese Application No. 2005-096011, filed Feb. 28, 2005; the entire contents of each of which are incorporated herein.

TECHNICAL FIELD

The present invention relates to a cultured cell sheet, a production method, and an applied tissue repair method thereof, in medical and biological fields, etc.

BACKGROUND ART

Japan is becoming an aging society with the highest average life expectancy in the world. People are beginning to place more emphasis on living better, i.e., "the quality of life (QOL)", rather than merely prolonging life. Under such circumstances, medical techniques are rapidly progressing, and techniques for reconstruction of organs damaged by trauma or disease are also advancing remarkably. Therefore, in recent years, a lot of attention has been focused on regenerative medical techniques in which organ tissue is reconstructed in the cell culture system employing cultured cells, and then transplanted to the target site.

To carry out such treatments, it is necessary to use tissue adhesive agents for tissue adhesion. The tissue adhesive agents currently used in the clinical field have been broadly classified into cyanoacrylate adhesive agents, gelatin-aldehyde adhesive agents, and fibrin glue adhesive agents. Cyanoacrylate adhesive agents employ adhesiveness by a polymerization reaction of the agents' cyanoacrylate monomers, and are superior in adhesive intensity and bonding speed. However, cyanoacrylate adhesive agents are synthetic agents which are not originally endogenous, and prevent healing by producing formaldehyde by hydrolyzation of a cured monomer, which causes toxicity to living organisms. Therefore, the problems exist that the site to be applied was limited, and the adhesive agents should not be applied to a site near a central nerve or blood vessel. Gelatin-aldehyde adhesive agents employ adhesiveness by a cross-linking reaction between a gelatin (biopolymer of the degenerated collagen) and formaldehyde or glutaraldehyde. However, the gelatin-aldehyde adhesive agents are also synthetic agents that are not endogenous. Although the gelatin-aldehyde adhesive agents also have sufficiently high adhesive intensity, since toxic aldehyde compounds are employed as a cross-linking agent, they are also biologically toxic. On the other hand, fibrin glue adhesive agents are made from a tissue-derived material, which employs adhesiveness by a reaction of blood coagulation. Although this type of adhesive agent is less toxic than the above described synthetic adhesive agents, the adhesiveness is low, and large amounts of fibrin glue should be used, since the fibrin glue itself is metabolized in vivo. Further, recently, some problems are being indicated relating to the topical inflammation at the site where the adhesive agent has been applied, since the fibrin glue is prepared and purified heterogeneously or the mechanisms of the adhesiveness of the fibrin glue are the same as the blood coagulation reaction.

Technology that provides a cell sheet having sufficient basal membrane-like proteins has been proposed. Conventionally, cell culture is conducted on a glass surface, or on the surface of a synthetic polymer compound along with a variety of surface processing. In order to achieve this, for example, various types of vessels made of polystyrene subjected to surface processing such as silicone coating, gamma irradiation, etc., are commonly used as vessels for cell culture. Cells that have been cultured and grown with these types of cell culture vessels, are detached and harvested from the surface of the vessel by a chemical agent treatment or a proteinase treatment such as trypsin. However, in cases where the cells are harvested by the above-mentioned chemical agent treatment, some disadvantages have been pointed out: the treatment method is cumbersome and complicated; the potential for contamination by impurities is increasing; and examples of defects, in which cells are caused to degenerate or are damaged by the chemical treatment, and lose their original function.

Thus far, in order to overcome the above-mentioned disadvantages, a number of techniques have been proposed by the present inventors. Especially, in Japanese Patent Application No. 2001-226141, a method for producing a cultured cell sheet which comprises steps of coating the surface of the cell culture support with a temperature responsive polymer having a lower or upper critical solution temperature ranging from 0° C. to 80° C. in water, having the cultured cell layers multi-layered by way of a conventional method, as necessary, and detaching the cultured cell sheet only by changing the temperature of the culture support. As a result of application of this method, a cultured cell sheet having sufficient strength can be produced. Furthermore, a thus obtained cultured cell sheet also retains basal membrane-like proteins, and also has improved adhesiveness to tissue, when compared with a cell sheet harvested using the above described dispase treatment. Moreover, PCT International Publication No. WO 02/08387 discloses a method for producing a cultured myocardial cell sheet, which comprises steps of culturing the cells of myocardial tissue on a cell culture support having a support surface coated or covered with a temperature responsive polymer, preparing a myocardium-like cell sheet, and subsequently, adjusting a temperature of the culture medium to a temperature greater than the upper critical solution temperature or less than the lower critical solution temperature, bringing the layered cultured cell sheet into close contact with a polymer membrane, detaching the cultured intact cell sheet together with the polymer membrane, and three-dimensionally structuring by a predetermined method. As a result of application of this method, a myocardium-like cell sheet and a three-dimensional structure were discovered to be constructed in vitro with reduced structural defects and with some of the functions of myocardial tissue. Neither of Application No. JP 2001-226141 nor WO 02/08387 have investigated conferring the flexibility to the cell sheet, and have discussed the use as tissue repair material for suppressing the air leakage, blood leakage or bodily fluid leakage from the surface of an organ. However, the use of such a cultured cell sheet as a tissue adhesive can be employed for the patient receiving tissue repair with an extremely high degree of safety, because the cell sheet can be prepared from the cell of the patient himself and, therefore, is highly safe.

DISCLOSURE OF THE INVENTION

Problem(s) to be Solved

The present invention is intended to solve the above-mentioned problems in conventional technology. Specifically, a purpose of the present invention is to provide a cultured cell sheet with excellent tissue adhesiveness and excellent flexibility. Moreover, a purpose of the present invention is to provide a method for manufacturing the cultured cell sheet and application as tissue repair material for suppressing the air leakage, blood leakage or bodily fluid leakage from the surface of an organ.

Means for Solving the Problem(s)

The present inventors have conducted research and development, by investigating various aspects, in order to solve the above-mentioned problems. As a result, it was discovered that a highly adhesive cultured cell sheet with excellent tissue adhesiveness and application as tissue repair material for suppressing the air leakage, blood leakage or bodily fluid leakage from the surface of an organ was obtained by the steps of: culturing cells, such as fibroblasts, cells of alveolar tissue, or cells of myocardial tissue, on a cell culture support, the surface of which is coated with a temperature responsive polymer; and afterwards, adjusting a temperature of the culture medium to a temperature greater than the upper critical solution temperature or less than the lower critical solution temperature; and detaching the cultured cell sheet. The present invention was completed based on the above-mentioned knowledge.

Specifically, the present invention provides a highly adhesive cultured cell sheet with a superior adhesiveness to the surface of a leaking site on an organ and with an excellent flexibility.

The present invention provides a highly adhesive cultured cell sheet, which comprises a step of culturing at least one type of cell selected from the group consisting of: fibroblasts, cells of alveolar tissue, cells of myocardial tissue, cells of hepatic tissue, cells of vascular tissue, mesenchymal stem cells, and adipose derived cells, on a cell culture support having a surface of the support coated with a temperature responsive polymer having an upper or lower critical solution temperature ranging from 0° C. to 80° C. in water, and thereafter, comprising the steps of: adjusting the temperature of the culture medium to a temperature greater than the upper critical solution temperature or less than the lower critical solution temperature; bringing the cultured cell sheet in close contact with a carrier; and detaching the cultured cell sheet together with the carrier. The highly adhesive cultured cell sheet obtained in the above-mentioned manner demonstrates superior adhesiveness to the surface of a leaking site on an organ, and therefore, cultured cell sheets having superior adhesiveness, such as those of the present invention, are sometimes called, "highly adhesive cultured cell sheets".

Moreover, the present invention provides a cultured cell sheet for application as tissue repair material for suppressing air leakage, blood leakage or bodily fluid leakage from the surface of an organ.

In addition, the present invention provides a treatment method which is conducted by transplanting the highly adhesive cultured cell sheet to the site of air leakage, blood leakage or bodily fluid leakage from the surface of an organ.

Effect of the Invention

The highly adhesive cultured cell sheet obtained by the present invention has extremely high adhesiveness to a leaking site of the surface of an organ and an excellent flexibility. Therefore, the use of the cell sheet of the present invention enables to suppress air leakage, blood leakage or bodily fluid leakage from the surface of an organ. Consequently, the present invention is extremely useful in biological and medical fields, etc., such as cell engineering and medical engineering.

PREFERRED MODE FOR CARRYING OUT THE INVENTION

The present invention provides a cultured cell sheet which has superior adhesiveness to the surface of an organ and has an excellent flexibility. Suitable cells for producing the cultured cell sheet of the present invention may include any one type or combination of two or more types of cells selected from the group consisting of: fibroblasts, cells of alveolar tissue, cells of myocardial tissue, cells of hepatic tissue, cells of vascular tissue, mesenchymal stem cells, and adipose derived cells. However, the present invention is not strictly limited to the above-mentioned types of cells. In the present invention, the highly adhesive cultured cell refers to a sheet which is prepared by the steps of culturing each of the above-mentioned types of cells as a single layer on the surface of the culture support, and then, detaching the cell sheet from the support. Thus obtained cell sheet has a lower side surface which is contacted to the culture support at the time of culture, and an upper side surface on the opposite side thereof. If the cells are cultured on the cell culture support, the surface of which is coated or covered with a temperature responsive polymer having an upper or lower critical solution temperature ranging from 0° C. to 80° C. to in water indicated in the present invention, there will be an abundance of adhesive proteins produced on the lower side surface of the cell sheet at the time the cells are cultured.

The cultured cell sheet of the present invention may or may not include a scaffold other than that produced by the cultured cells, such as collagen, fibronectin, laminin, etc. However, it is not particularly limited.

The cultured cell sheet of the present invention is constructed of at least one type or a combination of two or more types of cells selected from the group consisting of: fibroblasts, cells of alveolar tissue, cells of myocardial tissue, cells of hepatic tissue, cells of vascular tissue, mesenchymal stem cells, and adipose derived cells. These cells are cells that are capable of expressing phenotype of the various types of chondroid tissue mentioned above.

The highly adhesive cultured cell sheet of the present invention adheres extremely well to the leaking site of the surface of an organ. The high adhesiveness of the cultured cell sheet is achieved by maintaining its flexibility and reducing the shrinkage of the cultured cell sheet that is detached from the surface of the culture support.

The flexibility as demonstrated by the present invention is such that, after tissue has been covered by the cultured cell sheet, the above-mentioned cultured cell sheet obstructs the performance of the tissue no more than 20%, preferably no more than 10%, and even more preferably no more than 8%. The highly adhesive cultured cell sheet of the present invention adheres extremely well to the site of the leakage on the surface of the body tissue. In cases where the cultured cell sheet that is covering the tissue is rigid, the performance of the tissue is obstructed more than 20%, and the organ cannot exhibit the intact function thereof.

Regarding the suppression of the shrinkage of the cultured cell sheet, a percentage of shrinkage of the cultured cell sheet when detached from the surface of the culture support is preferably no more than 20%, more preferably no more than 10%, and even more preferably no more than 5%, in either of the lengthwise directions of the sheet. If the percentage of shrinkage is no less than 20%, the detached cell sheet becomes flaccid, and unable to adhere to living tissue well, even when attached to the living tissue. As a result, the detached cell sheet with no less than 20% shrinkage demonstrates the characteristics of the highly adhesive cell sheet of the present invention.

A method for preventing the cultured cell sheet from shrinking is not particularly limited in any way, and includes a method comprising the steps of bringing a ring-shaped carrier with a center portion cutout in close contact with the above-mentioned cell sheets at the time of detaching the cultured cell sheet from the culture support, and detaching the cell sheet with the above-mentioned carrier.

The carrier that is used when detaching the highly adhesive cultured cell sheet has a structure for keeping the cell sheet of the present invention from shrinking, and a carrier such as that made of a polymer membrane, or a structure formed from a polymer membrane, or a metallic fixture, etc., may be used. For example, in cases where a polymer is used as the carrier material, polyvinylidene difluoride (PVDF), polypropylene, polyethylene, cellulose and derivatives thereof, papers, chitin, chitosan, urethane, etc., may be used as the specific material of the carrier.

In the case of the present invention the term "close contact" hereinafter refers to having the cell sheet in a state in which it does not slip or slide on the carrier, in order to prevent the cell sheet from shrinking at the boundary between the cell sheet and carrier, and therefore, it may be in close contact by being physically bonded, or it may be in close contact via the fluid (for example, the culture medium, and other isotonic solutions) existing between each of the cell sheet and the carrier.

The shape of the carrier is not specifically limited in any way. For example, when transplanting the highly adhesive cultured cell sheet obtained, if a cut out portion of the carrier which is the same size or larger than the transplantation site is utilized, greater convenience results since the cell sheet is only fixed to the portion surrounding the cutout portion, and only a cell sheet with a cut-out portion that fits the transplantation site can be transplanted.

The highly adhesive cultured cell sheet of the present invention may be provided as a monolayered sheet, or as a layered sheet. Here, the layered sheet can be prepared by layering sheets consisting solely of the highly adhesive cultured cell sheet or may be prepared by combining the highly adhesive cultured cell sheet with a sheet of other cells. For example, a cell sheet includes, but is not limited to, one which is prepared by layering the above-mentioned fibroblast cell sheet and another fibroblast cell sheet, or a cell sheet that is prepared by layering of a fibroblast cell sheet and a cell sheet derived from cells other than those of the fibroblast cell sheet (for example, a cell sheet made of cells of alveolar tissue), etc. In such cases, if at least two different types of cells are employed, the different cells intercellularly interact with each other, and therefore, a cell sheet having the characteristic of even higher activity can be obtained. Furthermore, a position where the cell sheet is layered, the order of the layered cell sheets, and the number of the layered cell sheets are not particularly limited in any way. However, depending on the covered tissue, the structure of the layered sheet may be varied, by employing a highly adhesive cell sheet on the uppermost layer, and so on. Furthermore, the number of the layered cell sheets is preferably no more than 10, more preferably no more than 8, and even more preferably no more than 4. The fibroblasts may also be viable even in an environment in which basic nutrients are not fully supplied. However, a cell sheet consisting of more than 10 layers of cell, sheets is undesirable, since it is difficult to deliver oxygen and nutrients to the center portion of the layered cell sheets.

For example, the layered sheet of the present invention can be produced by employing a method, for example, but not limited to, the one described below:

(1) a method of superimposing the highly adhesive cultured cell sheet in close contact with the above-mentioned carrier by the steps of attaching the first cell sheet in close contact with the carrier to the cell culture support, and afterwards, removing the carrier off the first cell sheet by the addition of a culture medium, and layering the second cell sheet by attaching the second cell sheet in close contact with a carrier, and repeating the steps;

(2) a method of superimposing the highly adhesive cultured cell sheet in close contact with the above-mentioned carrier by the steps of inverting the first cell sheet in close contact with the carrier, fixing the carrier side of the first cell sheet to the surface of the cell culture support, attaching a second cell sheet to the cell sheet side of the first cell sheet, removing the carrier off the first cell sheet by adding culture medium afterwards, and repeating the steps by attaching another separate cell sheet;

(3) a method in which two cell sheets each in close contact with a carrier are brought into close contact with each other at the cell sheet side; and (4) a method in which the cell sheet in close contact with the carrier is fitted to an affected area of the individual, and after the cell sheet is attached to living tissue, removing the carrier, and overlaying another separate cell sheet on the affected area.

The highly adhesive cultured cell sheet of the present invention is characterized in that the basal membrane-like proteins between the cell and support formed during the culture are not damaged by enzymes, such as proteinases like dispase, trypsin, etc. Therefore, in order to produce a cultured cell sheet with such a characteristic, the cell culture is preferably conducted on a surface of the cell culture support coated with a temperature responsive polymer.

The temperature responsive polymer that is used to coat the cell culture support has upper or lower critical solution temperature ranging from 0° C. to 80° C. in water, and more preferably a temperature ranging from 20° C. to 50° C. in water. An upper or lower critical solution temperature that exceeds 80° C. is not preferable, since cells may die. Furthermore, an upper or lower critical solution temperature that is lower than 0° C. is also not preferable, since it typically causes an extreme decrease in cellular growth rate or causes cell death.

The temperature responsive polymer to be used in the present invention may be either a homopolymer or a copolymer. Examples of such a polymer may include, for example, the polymer disclosed in Japanese Patent Publication No. H2-211865 (JP 2-211865 A). Specifically, for example, they may be obtained by polymerization or copolymerization of the monomer mentioned below. Monomers that can be used include, for example, (meth)acrylamide compound, N- (or N,N-di)alkyl substituted (meth)acrylamide derivative, or a vinyl ether derivative; in the case of a copolymer, at least two of these monomers may be selected and used. Moreover, those monomers may be copolymerized with other monomers, or polymers may be grafted together or copolymerized, or alternatively, mixtures of polymers and copolymers may be employed. If desired, the polymers may be crosslinked to an extent that does not impair their properties.

The support that is to be covered with the temperature responsive polymer may be chosen from among the glass, modified glass, compounds such as polystyrene and poly(methyl methacrylate), and all other substances that can generally be shaped, as exemplified by polymer compounds other than those compounds, and ceramics.

The method of covering the support with the temperature responsive polymer is not limited in any particular way but one may follow the methods described in JP 2-211865 A. Specifically, the coating operation can be achieved by either subjecting the support and the above-mentioned monomers or polymers to electron beam (EB) exposure, γ-ray irradiation, ultraviolet irradiation, plasma treatment, corona treatment or organic polymerization reaction or by means of physical adsorption as effected by application of coating solutions or the kneading step.

The coating of the temperature responsive polymer is suitably in the range of 0.5 to 5.0 μg/cm$^2$, preferably 1.0 to 4.0 μg/cm$^2$, and more preferably 1.2 to 3.5 μg/cm$^2$. If the coverage of the temperature responsive polymer is less than 0.5 μg/cm$^2$, the cells on the polymer will not easily detach even if they are given a stimulus and the operating efficiency is considerably lowered, which is not preferable. If, on the other hand, the coverage of the temperature responsive polymer is greater than 5.0 μg/cm$^2$, cells will not easily adhere to the covered area and adequate adhesion of the cells becomes difficult to achieve. The shape of the culture support of the present invention may include, for example, but is not particularly limited to, a dish shape, multi-plate shape, flask shape, cell-insert shape, etc., may be employed.

The composition of the culture medium for culturing the above-mentioned cells of the present invention is not particularly limited in any way, and any conventionally used may be employed at the time the above-mentioned cells are cultured. In the cases that fibroblasts, cells of alveolar tissue, cells of myocardial tissue, cells of hepatic tissue, cells of vascular tissue, mesenchymal stem cells, and adipose derived cells are cultured, the culture medium may be prepared by, for example, supplementing an α-MEM culture medium, an F-12 culture medium, DMEM culture medium, or any mixture thereof, with 10% to 20% bovine serum, or optionally with 50 μg/ml of ascorbic acid 2-phosphate in addition to bovine serum.

Moreover, the cultured cell sheet of the present invention is highly flexible, and this flexibility is achieved by culturing cells under specific culture conditions. However, the method thereof includes, for example, but is not limited to, a method where a surfactant protein is added to the culture medium, a method where alveolar cells which produce the surfactant protein are co-cultured, a method where β-aminopropylnitrile is added to the culture medium, or a method where other types of collagen cross-linking inhibitor is added to the culture medium. In cases where any one of the methods where a surfactant protein, β-aminopropylnitrile, or other type of collagen cross-linking inhibitor is added is used, the concentration thereof added to the culture medium is preferably at least 10 μM, more preferably at least 100 μM, and even more preferably at least 200 μM. Moreover, since the cell sheet is not flexible when additive concentration is less than 10 μM, and the shape of the cell sheet cannot be retained when the additive concentration is greater than 500 μM, neither of these additive concentrations is desirable.

The temperature of the culture medium is not particularly limited, as long as the temperature is below the upper critical solution temperature, or above the lower critical solution temperature of the polymer that is coated onto the surface of the support. However, it should be appreciated that a low temperature, where cultured cells can not proliferate, or high temperature region, where cultured cells undergo cell death, is of course unsuitable. Culture conditions other than temperature are not particularly limited, and conventional procedures may be followed. For example, a culture medium used may be a culture medium to which a serum such as common fetal bovine serum (FCS) has been supplemented, or a serum-free culture medium, to which no serum has been added.

When detaching and harvesting the cultured cells from the cultured support material by the method of the present invention, the highly adhesive cultured cell sheet in close contact with the carrier can be removed by the steps of bringing the cultured cell sheet in close with the carrier, adjusting the temperature of the culture support attached to the cells to a temperature above the upper critical solution temperature, or below the lower critical solution temperature of the polymer coating the culture support, increasing the hydrophilicity of polymer coating the surface of the support, and detaching the cultured cell sheet in close contact with the carrier from the culture support, due to weakening of the attachment between the culture support and the cultured cell sheet. Moreover, the sheet may be detached either in the culture medium which is used to culture the cells, or in another isotonic solution, depending on the purpose.

In order to detach and harvest the highly adhesive cultured cell sheet at a high yield, a method in which the cell culture support is lightly tapped and shaken, or a method in which the culture medium is agitated using a pipet, etc., may be used alone, or in combination. In addition, when required, cultured cells may be washed with isotonic solution, prior to detaching and harvesting.

The highly adhesive cultured cell sheet of the present invention, when harvested in the above-mentioned manner, are not damaged by proteinases like dispase, trypsin, etc., from the time of culture to the time of detachment of the cell sheet. Therefore, the highly adhesive cell sheet which has been detached from the support retains the intercellular desmosome structure, has only a few structural defects, and exhibits high strength. Furthermore, the basal membrane-like proteins of the sheet of the present invention between the cell and support formed at the time of culture are not damaged by enzymes, thus providing superior adhesion to affected area at the time of transplantation, and allowing implementation of a very effective treatment to be possible. More specifically, in cases where conventional proteinases such as trypsin are used, the intercellular desmosomal structure and the basal membrane-like proteins between the cell and support, etc., are not retained at all; and therefore, the cells are detached from the culture support in a individually separated condition. Although it is commonly known that, among proteinases, dispase can allow for detachment with about 10% to 60% of the retained intercellular desmosomal structure, the basal membrane-like proteins between the cell and support, etc., are almost completely damaged, and the cell sheet obtained has only low strength. However, the cell sheet of present invention keeps no less 80% of the desmosomal structure and basal membrane-like proteins intact, and therefore, provides the various effects described above.

The leakage site of the surface on the organ is not particularly limited as long as it is a site at which air, blood, or bodily fluid is leaking from the organ surface. Examples of the leakage site of the surface on the organ include the site of air leakage from lung tissue and the site of bleeding from vascular tissue or liver tissue. The utilization of the highly adhesive cultured cell sheet of the present invention for the surface of the leakage site may include, for example, but is not particularly limited to, a method in which the affected area is covered with the highly adhesive cultured cell sheet of the present invention. In such cases, the cultured cell sheet may be cut to appropriately fit the size and shape of the affected area. In this way, the highly adhesive cultured cell sheet of the present invention is able to adhere extremely well to the surface of leakage site on an organ surface, which cannot be achieved by the prior art.

A method for fixing the highly adhesive cultured cell sheet to the surface of an organ as demonstrated by the present invention is not particularly limited in any way, and therefore, the cell sheet may be sutured to living tissue, may be connected to living tissue with an adhesive agent capable of being used in vivo, or may only be attached to the affected area without using either of these means, in order to quickly graft the highly adhesive cultured cell sheet to living tissue as shown by the present invention.

An application of the highly adhesive cultured cell sheet as shown in the present invention is effective, for example, but not particularly limited to, in treatments of the air leakage from lung tissue and the bleeding from vascular tissue or liver tissue.

In cases where the cultured cell sheet of the present invention is used in transplantation to the surface of an organ, the cultured cell sheet is transplanted by removing the cell sheet off the carrier, after fitting the cell sheet to the affected area. The method for removing the cell sheet off the carrier include, for example, but not particularly limited to, a method of removing the cell sheet off the carrier by wetting the carrier in order to weaken the adhesiveness, or a method of cutting the cultured cell sheet using a cutting tool such as a scalpel, forceps, a laserbeam, a plasma wave, etc. For example, in cases where a cell sheet is in close contact with a carrier with a center portion cutout is employed, it is preferable to cut the cultured cell sheet to be transplanted with a laserbeam, or the like, along the border of the affected area, since it is possible to avoid attachment of the cultured cell sheet to an undesired area outside of the affected area.

The highly adhesive cultured cell sheet obtained by the method mentioned above is superior when compared with one obtained by conventional methods, due to the noninvasiveness of the cultured cell sheet at the time of detachment, and therefore, the clinical applications for the leakage site of the tissue for transplantation, etc., are very promising. Especially, the highly adhesive cultured cell sheet of the present invention shows higher adhesiveness to living tissue than a conventional transplantation cell sheet, and grafts to living tissue very rapidly.

Moreover, antigenic and infective problems can be solved due to the use of autologous cells. With respect to the fixation of the cultured cell sheet to the leakage site on the surface of an organ, since the cultured cell sheet of the present invention is non-invasively harvested together with the extracellular matrix including the adhesion molecules secreted by the cultured cell sheet, which is transplanted, the cultured cell sheet has an advantage in early establishment of the leakage site on the surface of an organ to be transplanted when it is transplanted to the surface. Therefore, the present invention provides an extremely effective technology with improvements in the treatment efficiency of the affected area, and further alleviation of a burden on a patient.

EXAMPLES

Hereinafter, the present invention will be explained in further detail based on the following Examples, which are not intended to limit the scope of the present invention in any way.

Examples 1 and 2

To a commercial culture dish with a diameter of 3.5 cm (Falcon 3001, manufactured by Becton Dickinson Labware), 0.07 ml of the solution of N-isopropyl acrylamide monomer dissolved in isopropyl alcohol at a concentration of 53% (Example 1) or 54% (Example 2) was applied. The culture dish was exposed to electron beams at an intensity of 0.25 MGy, and the N-isopropyl acrylamide polymer (PIPAAm) was immobilized on a surface of the culture dish. After irradiation, the culture dish was washed with ion-exchanged water to remove a residual monomer and the PIPAAm that did not bind to the culture dish, was then dried inside a clean bench, and sterilized by ethylene oxide gas, to obtain a cell culture support material coated with a temperature responsive polymer.

Figure 1:
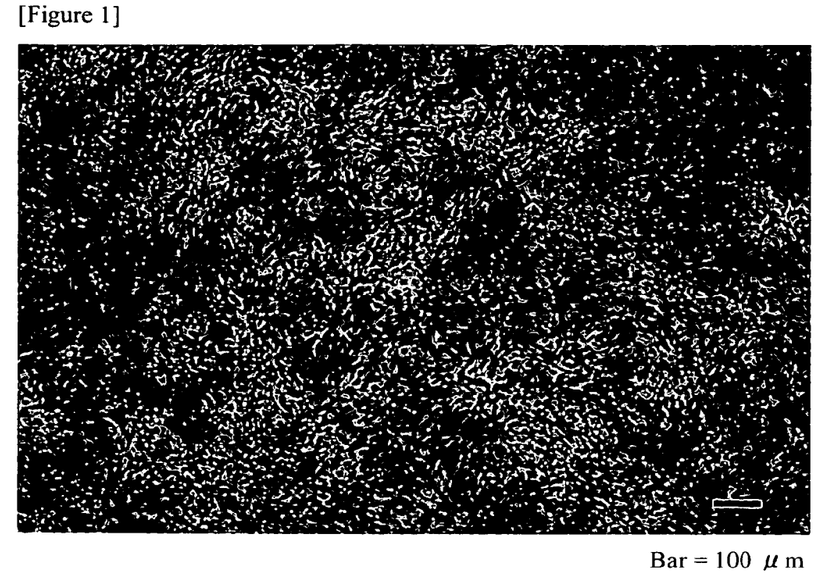
FIG. 1 shows a cultured cell sheet of alveolar cells 10 days after the start of the culture, as indicated in Example 2.

The amount of the temperature responsive polymer on the support surface was measured. As a result, it was found that the supports' surface was coated with the temperature responsive polymer in an amount of 1.7 µg/cm$^2$ (Example 1), and 1.9 µg/cm$^2$ (Example 2), respectively. A lung tissue was extracted from a GFP-transgenic neonatal rat, and the cells were isolated with collagenase. Three days after the start of culture, the cells were subcultured on the above described cell culture support material, and the cell culture support was cooled for 30 minutes at 20° C. to harvest the cell sheet of the fourth passage. The cell sheet at the time of harvest is shown in FIG. 1.

The harvested cell sheet was layered, and was applied to closing of air leakage. An air leakage model was prepared as follows: an 8 week old F-344 nude rat was anesthetized intraperitoneally and placed on an artificial ventilator after endotracheal intubation; the left posterior lateral side of the anesthetized rat was excised; the thorax was opened at the fourth intercostal space; the lung-pleura region was excised approximately 3 cm; and the air leakage was confirmed with a Minute Volume of 400 cc. The air leakage site was then covered with a double-layered cell sheet, the artificial ventilator was restarted after 5 minutes of respiratory arrest, the Minute Volume was increased 100 cc every 5 minutes to a maximum of 1000 cc, and the degree of adhesion of the cell sheet, and the presence or absence of air leakage were evaluated.

Figure 2:
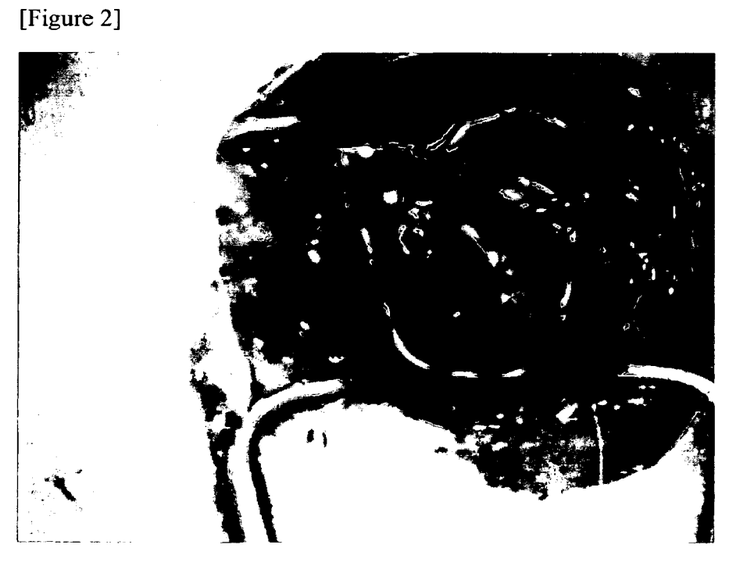
FIG. 2 is a photograph showing the appearance of an air leakage model, as indicated in Example 2.
Figure 3:
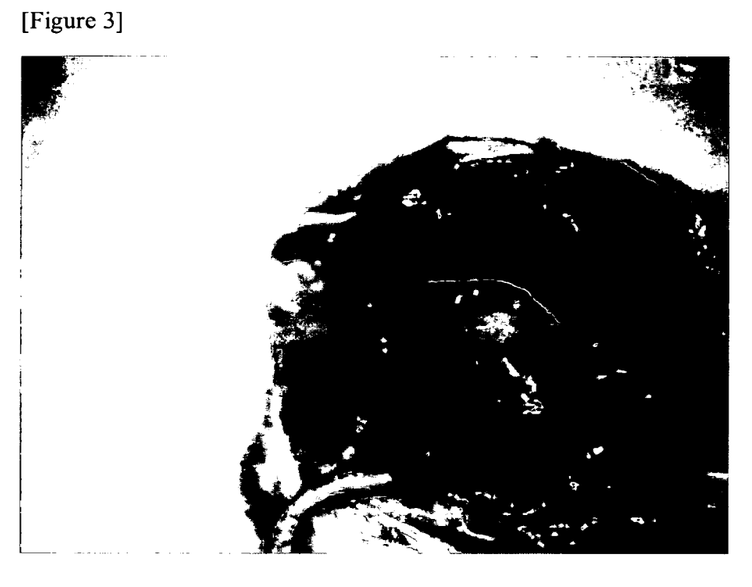
FIG. 3 is a photograph showing the appearance of the cultured cell sheet adhered to the site of air leakage, as indicated in Example 2.
Figure 4:
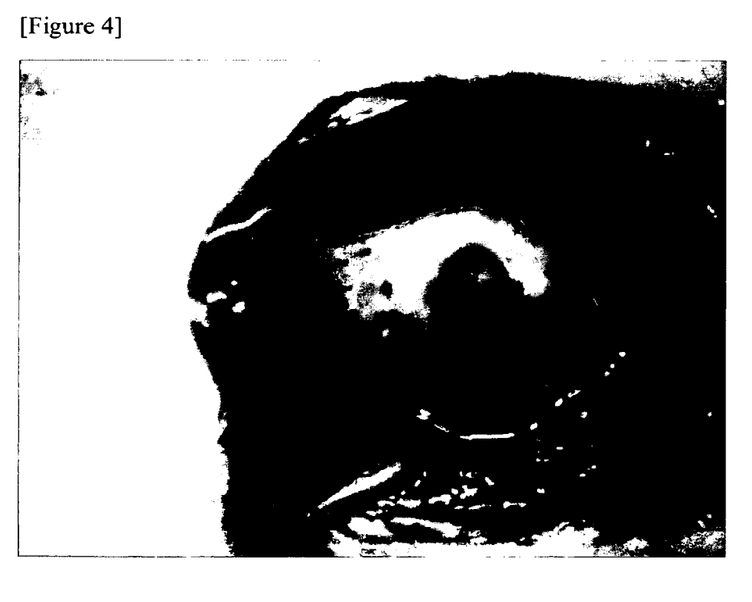
FIG. 4 is a photograph showing the appearance of the site of air leakage which was closed by the cultured cell sheet, as indicated in Example 2.
Figure 5:
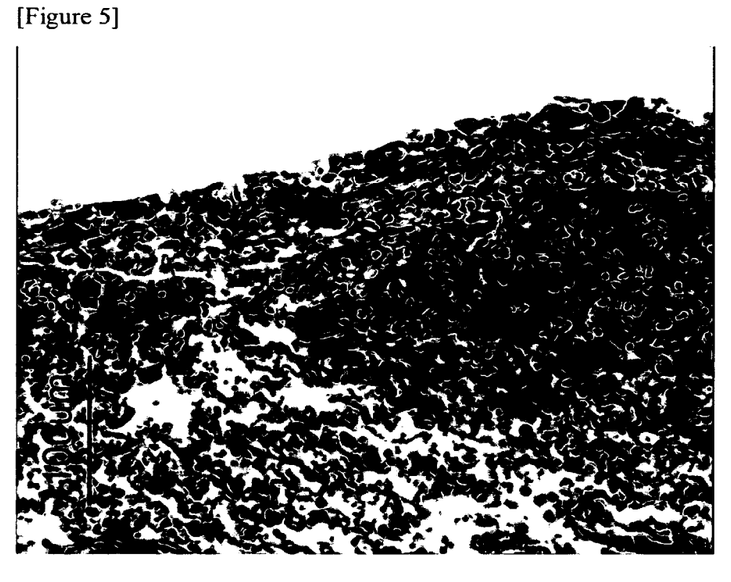
FIG. 5 is a photograph showing the results of a hematoxylin-eosin stained tissue section from the site of air leakage which was closed by the cultured cell sheet of the invention, as described in Example 2.

The results showed that the above-mentioned cultured cell sheet was attached to the air leakage site, was elongated and contracted in agreement with the artificial ventilator, and closed the air leakage site. The appearance is shown in FIGS. 2 to 4 (FIG. 2 shows the air leakage model, FIG. 3 shows the cultured cell sheet attached to the air leakage site, and FIG. 4 shows air leakage being closed by the cultured cell sheet, respectively). Moreover, a histological evaluation was conducted by a hematoxylin-eosin staining or an Azan staining of tissue sections of the tissue with the closed air leakage site. The results obtained are shown in FIG. 5 (hematoxylin-eosin stain), and FIG. 6 (Azan stain).

Figure 6:
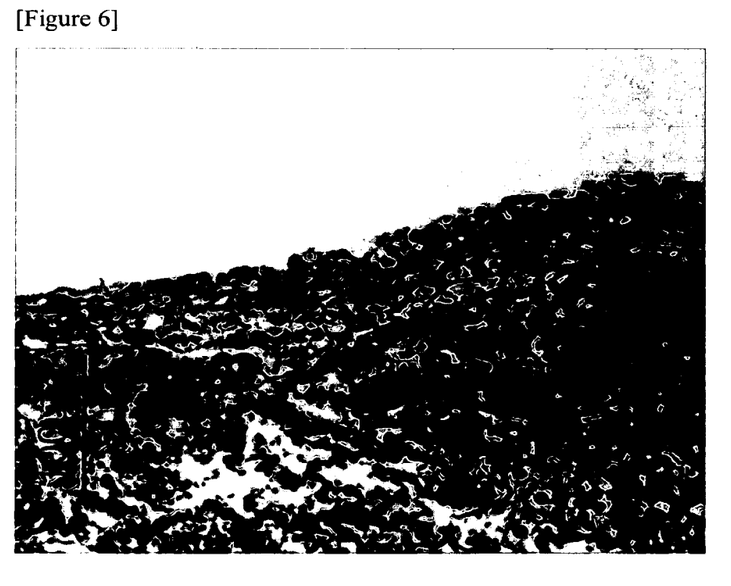
FIG. 6 is a photograph showing the results of an Azan stained tissue section from the site of air leakage which was closed by the cultured cell sheet of the invention, as described in Example 2.

From both figures, it was clear that the cultured cell sheet used for covering the leakage site was in close contact with the surface of the tissue around the air leakage site. Therefore, the usefulness of the cultured cell sheet as a tissue repair material could be confirmed.

Example 3

The study of this example is conducted in a similar manner to that of Example 2, except that 250 W β-aminopropylnitrile was added to the culture medium, when cell passage was started on the cell culture support material, 3 days after the start of culture in Example 2. The cultured cell sheet obtained in the presence of β-aminopropylnitrile was mechanically flexible. The air leakage site was closed, and contracture of the covered portion of the cultured cell sheet was not found. Accordingly, the usefulness of a cultured cell sheet having flexibility as a tissue repair material could be confirmed.

Example 4

A lung tissue was extracted from a GFP-transgenic neonatal rat, and the cells were isolated with collagenase, in a manner similar to that of Example 2. Three days after the start of culture, the cells were subcultured on the above described cell culture support material, and the cell culture support was cooled for 30 minutes at 20° C. to harvest the cell sheet of the fourth passage.

The harvested cell sheet was layered, and was applied to closing the bleeding site of the liver. A model for a bleeding site of the liver was prepared as follows: an 8 week old F-344 nude rat was anesthetized intraperitoneally and placed on an artificial ventilator after endotracheal intubation; the abdominal area of the anesthetized rat was excised; the surface layer of the liver was excised approximately 2 mm; and bleeding was confirmed. The site of bleeding was then covered with a double-layered cultured cell sheet, and the degree of adhesion of the cell sheet, and the presence or absence of bleeding were evaluated.

Figure 7:
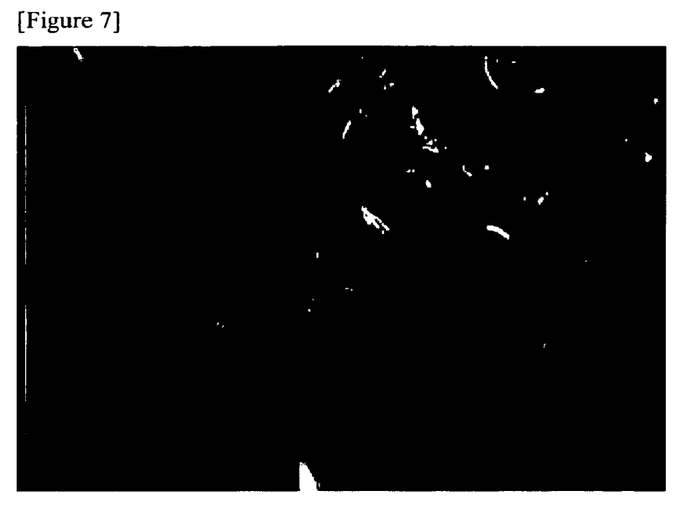
FIG. 7 is a photograph showing the appearance of a bleeding model, as indicated in Example 4.
Figure 8:
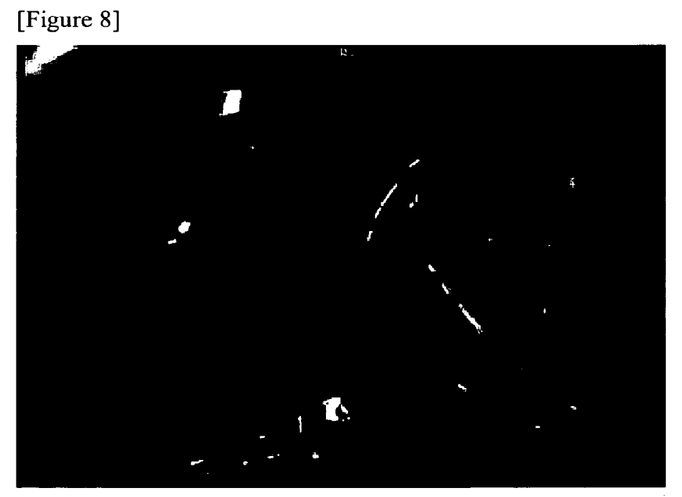
FIG. 8 is a photograph showing the appearance of a site of bleeding which was closed by the cultured cell sheet, as indicated in Example 4.
Figure 9:
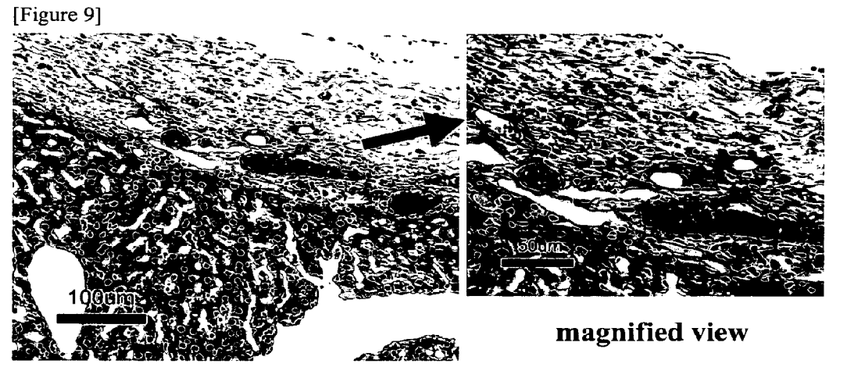
FIG. 9 is a photograph showing the results of a hematoxylin-eosin stained tissue section from a site of bleeding of the liver which was closed by the cultured cell sheet, 4 weeks after transplantation, as indicated in Example 4.

The results showed that the above-mentioned cultured cell sheet was attached to the bleeding site, and that the bleeding site was closed. The appearance is shown in FIGS. 7 and 8 (FIG. 7 shows the bleeding model, and FIG. 8 shows the cultured cell sheet attached to the bleeding site, respectively). Moreover, a histological evaluation was conducted by a hematoxylin-eosin staining or an Azan staining of tissue sections of the tissue with the closed bleeding site of the liver four weeks after transplantation for closing the bleeding site. The results obtained are shown in FIG. 9 (hematoxylin-eosin stain), and FIG. 10 (Azan stain).

Figure 10:
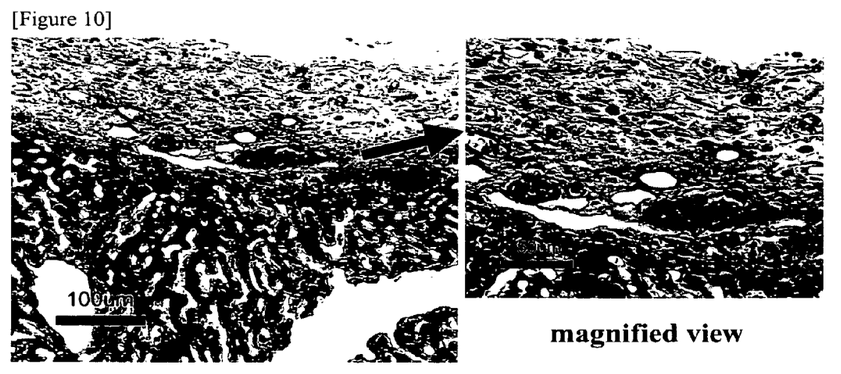
FIG. 10 is a photograph showing the results of an Azan stained tissue section from a site of bleeding in the liver which was closed by the cultured cell sheet of the invention, 4 weeks after transplantation, as indicated in Example 4.

From both figures, it was clear that the cultured cell sheet used for covering the bleeding site was in close contact with the surface of the tissue around the bleeding site. Therefore, the usefulness of the cultured cell sheet as a tissue repair material could be confirmed.

Example 5

A lung tissue was extracted from a GFP-transgenic neonatal rat, and the cells were isolated with collagenase, in a manner similar to that of Example 1. Three days after the start of culture, the cells were subcultured on the above-described cell culture support material, and the cell culture support was cooled for 30 minutes at 20° C. to harvest the cell sheet of the fourth passage.

The harvested cell sheet was layered, and was applied to closing the bleeding site of the blood vessel. A model for a bleeding site of a blood vessel was prepared as follows; an 8 week old F-344 nude rat was anesthetized intraperitoneally and placed on an artificial ventilator after endotracheal intubation; the abdominal area of the anesthetized rat was excised; a blood vessel was excised with a suture needle; and bleeding was confirmed. The site of bleeding was then covered with a double-layered cultured cell sheet, and the degree of adhesion of the cell sheet, and the presence or absence of bleeding were evaluated.

Figure 11:
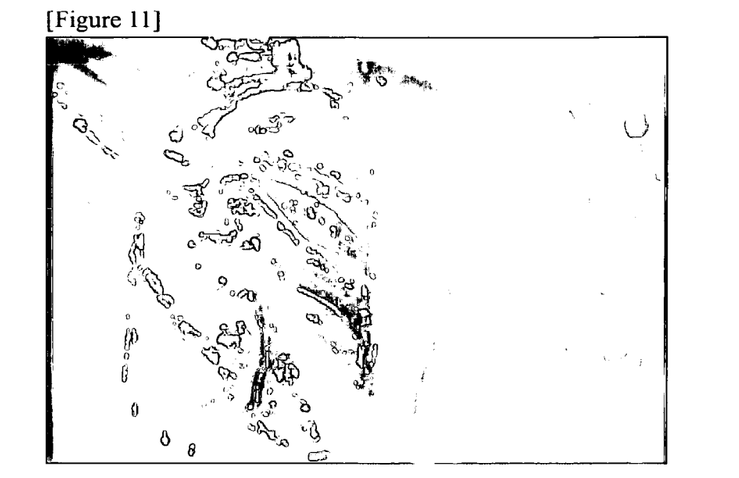
FIG. 11 is a photograph showing the appearance of a bleeding model, as indicated in Example 5.
Figure 12:
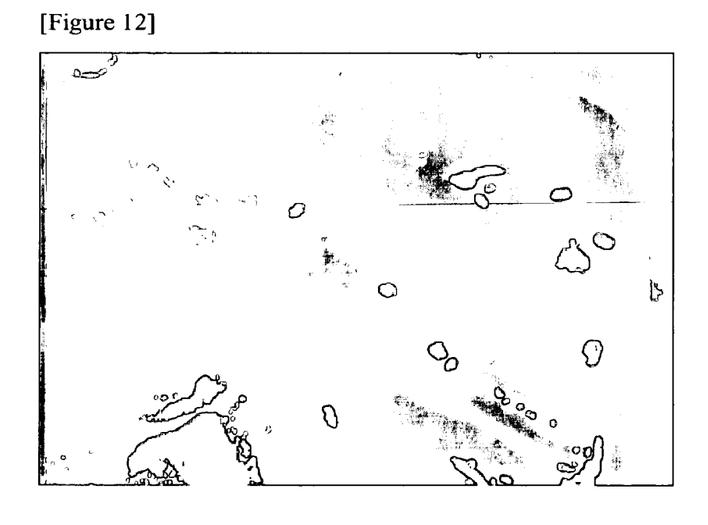
FIG. 12 is a photograph showing the appearance of a site of bleeding which was closed by the cultured cell sheet, as indicated in Example 5.

The results showed that the above-mentioned cultured cell sheet was attached to the bleeding site of the blood vessel, and that the bleeding from the site was stopped. The appearance is shown in FIGS. 11 and 12 (FIG. 11 shows the bleeding model, and FIG. 12 shows the cultured cell sheet attached to the bleeding site, respectively).

From both figures, it was clear that the cultured cell sheet used for covering the bleeding site was in close contact with the surface of the tissue around the bleeding site. Therefore, the usefulness of the cultured cell sheet as a tissue repair material could be confirmed.

INDUSTRIAL APPLICABILITY

The highly adhesive cultured cell sheet obtained by the present invention has extremely high adhesiveness to the leakage site of the surface the surface of an organ, and an excellent flexibility. The use of the cell sheet of the present invention enables suppression of air leakage, blood leakage or bodily fluid leakage from the surface of an organ. Therefore, the present invention is very promising in its clinical applications to air leakage from alveolar tissue or bleeding from blood vessel tissue or liver tissue, etc. Consequently, the present invention is extremely useful in biological and medical fields, etc., such as cell engineering and medical engineering.

The invention claimed is:

1. A method of treatment for suppressing air leakage from a surface layer of an organ comprising alveolar tissue; the method comprising transplanting to the organ in a subject in need thereof an autologous cultured cell sheet, which has tissue adhesiveness and flexibility; wherein said cultured cell sheet is obtained by culturing autologous fibroblast cells in a culture medium, wherein the cultured cells do not include cells of alveolar tissue, on a cell culture support having a surface coated with a temperature responsive polymer having an upper or lower critical solution temperature of 0° C. to 80° C. in water, in the range of 1.2 μg/cm$^2$ to 3.5 μg/cm$^2$; and wherein the transplanted cultured cell sheet obstructs performance of the tissue not more than 20% after the tissue has been transplanted with the cultured cell sheet.

2. The method according to claim 1, wherein transplantation is performed by covering of the surface layer of an affected area of the organ.

3. The method according to claim 1 further comprising cutting the cultured cell sheet according to size and shape of an affected area, before covering of the surface layer of the affected area of the organ.

4. The method according to claim 1, wherein the flexibility results from addition of a surfactant protein to the culture medium, addition of β-aminopropylnitrile to the culture medium, addition of other types of collagen cross-linking inhibitor to the culture medium, or a combination thereof.

5. The method according to claim 1, wherein the treatment suppresses air leakage from lung tissue.

* * * * *